United States Patent
Heaven et al.

[11] Patent Number: 5,611,803
[45] Date of Patent: Mar. 18, 1997

[54] TISSUE SEGMENTATION DEVICE

[75] Inventors: Malcolm D. Heaven, Hopewell; Michael Ko, Plainsboro, both of N.J.

[73] Assignee: Urohealth Systems, Inc., Costa Mesa, Calif.

[21] Appl. No.: 361,493

[22] Filed: Dec. 22, 1994

[51] Int. Cl.$^6$ .......................... A61B 17/22; A61B 17/36; A61B 17/38

[52] U.S. Cl. .................... 606/114; 606/113; 606/110; 606/47

[58] Field of Search .................... 606/113, 114, 606/106, 110, 127, 128, 45, 46, 47; 600/37; 128/749, 751

[56] References Cited

U.S. PATENT DOCUMENTS

| | | |
|---|---|---|
| 30,471 | 10/1860 | Lithomeldor . |
| 974,879 | 11/1910 | Gwinn . |
| 2,610,631 | 9/1952 | Calicchio . |
| 3,409,014 | 11/1968 | Shannon . |
| 3,476,114 | 11/1969 | Shannon et al. . |
| 3,476,115 | 11/1969 | Graeff et al. . |
| 3,665,926 | 5/1972 | Flores . |
| 4,177,813 | 12/1979 | Miller et al. . |
| 4,823,793 | 4/1989 | Angulo et al. . |
| 4,997,435 | 3/1991 | Demeter . |
| 5,037,379 | 8/1991 | Clayman et al. . |
| 5,074,867 | 12/1991 | Wilk . |
| 5,201,740 | 4/1993 | Nakao et al. ............................ 606/114 |
| 5,215,521 | 6/1993 | Cochran et al. . |
| 5,330,483 | 7/1994 | Heaven et al. . |
| 5,337,754 | 8/1994 | Heaven et al. . |
| 5,341,815 | 8/1994 | Cofone et al. ........................... 128/749 |
| 5,352,184 | 10/1994 | Goldberg et al. ......................... 606/37 |
| 5,397,320 | 3/1995 | Essig et al. . |
| 5,443,472 | 8/1995 | Li ............................................ 606/114 |
| 5,480,404 | 1/1996 | Kammerer et al. ...................... 606/113 |

*Primary Examiner*—Robert A. Hafer
*Assistant Examiner*—Benjamin Koo
*Attorney, Agent, or Firm*—Burns, Doane, Swecker & Mathis, L.L.P.

[57] ABSTRACT

A tissue segmentation device incorporated in an isolation bag for segmenting tissue during an operation such as in laparoscopic surgery. The device includes one or more loops of high strength wire which can be mechanically reduced in size to cut the tissue into smaller pieces. The wire loops can be heated electrically to aid in cutting through hard-to-cut parts of the tissue. The wire can be of a shape memory alloy which shrinks when heated to form a smaller diameter loop.

18 Claims, 7 Drawing Sheets

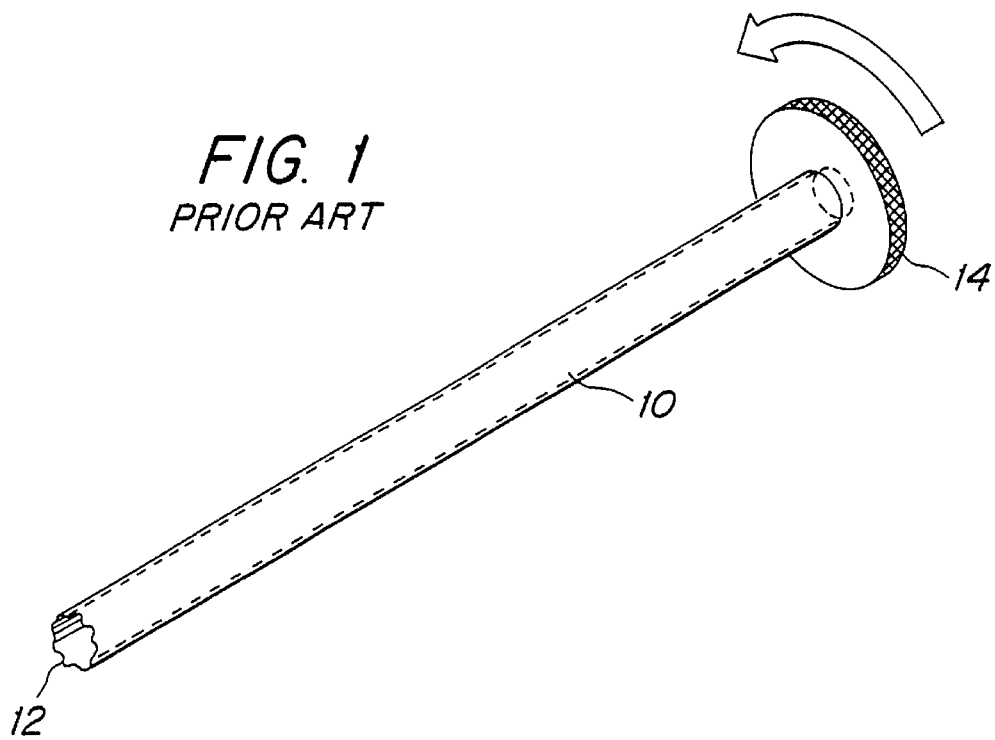
FIG. 1
PRIOR ART
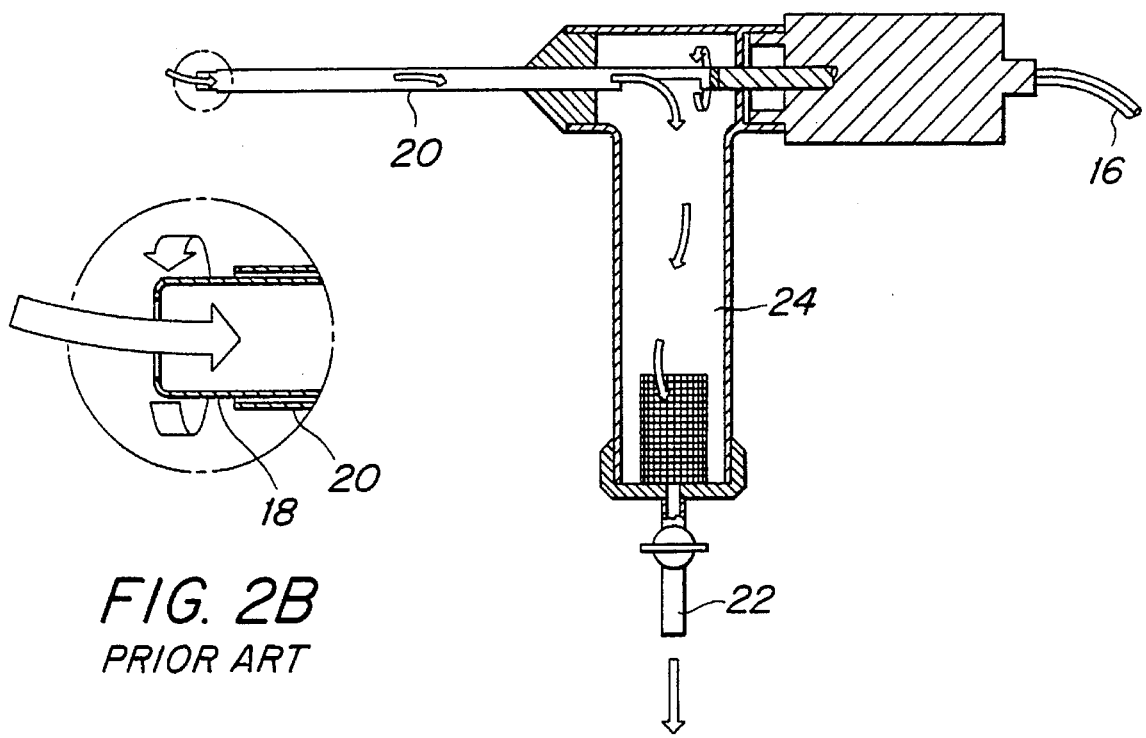
FIG. 2A
PRIOR ART
FIG. 2B
PRIOR ART

TISSUE SEGMENTATION DEVICE

BACKGROUND OF THE INVENTION

1. Field of the Invention

The invention relates to a medical device useful during minimally invasive procedures, such as laparoscopic procedures, for reducing the size of specimens so that they can be removed from a body by minimally invasive surgical techniques. The device further allows for the maintenance of sufficient tissue integrity to allow subsequent pathology.

2. Description of the Related Art

During the removal of a diseased gallbladder during cholecystectomy, an inflamed appendix during appendectomy, a kidney during nephrectomy, or other procedures requiring the removal of relatively large tissue masses, it is frequently necessary to remove objects that are larger than the cannula through which the procedure is being conducted. One method of reducing the size of such objects is to use a device such as a morcellator. A morcellator is used in conjunction with a suitable tissue isolation bag or container to mechanically reduce the size of the object by grinding, coring or shaving the object. The isolation bag can then either be wholly withdrawn from the site, or the neck of the bag can be externalized through the cannula or the puncture site and the now small pieces of tissue removed piece by piece. If such a device is not available, or is ineffective, the surgeon must increase the size of the hole through which he is working, which is not desirable. The available morcellators are generally very slow, which increases costs associated with the operating procedure, and frequently do not remove tissue in identifiable form, which does not allow later pathology. Such morcellators are exemplified by the hand device shown in FIG. 1, which is essentially a tubular structure 10 with a sharpened front edge 12 which is driven into a tissue sample in order to remove a core of tissue. The process of removing a core of tissue is repeated until the structure has been sufficiently reduced in size as to be extractable through the available opening. These hand operated devices are extremely slow and laborious.

A similar device for morcellating a tissue mass is shown in FIG. 2. The morcellator, has a power supply 16 for rotating a tubular cutter 18 within a concentric tube 20. This device requires a vacuum source 22 to suck the cored-out tissue into a receptacle 24. This device is awkward, slow, bulky, and requires ancillary equipment devoted to it alone. Therefore, this device is not always found in an operating room. The current invention offers a much improved method of tissue bulk reduction.

U.S. Pat. No. 5,037,379 discloses a surgical tissue bag for percutaneously debulking tissue. The debulking is performed by inserting the bag through an access sheath into a body cavity, inserting a surgically removed tissue mass through an open end of the bag, closing the end of the bag and pulling the closed end of the bag out of the body cavity. The end of the bag is then opened and morcellating or debulking of the tissue through the open end of the bag is performed while the remainder of the bag remains in the body cavity. The bag is made of flexible and foldable material and includes an inner layer of puncture resistant material such as nylon in either woven or solid layer form for resisting penetration by a surgical morcellating instrument. The outer layer of the bag is made of a moisture proof material such as plastisol.

U.S. Pat. No. 5,215,521 discloses an entrapment envelope having a means for opening and closing. The entrapment envelope is constructed of flexible, low fluid permeability materials having sufficient strength to contain morcellator entry, organ fragmentation and removal.

U.S. Pat. No. 5,337,754 discloses a tissue isolation bag which expands from a collapsed configuration to an expanded configuration when pressurized gas or liquid is supplied thereto.

U.S. Pat. No. 5,330,483 discloses a tissue reduction device which is thermally activated and is used in conjunction with a tissue isolation bag. The tissue reduction member is in an expanded condition at body temperature but shrinks to a smaller specimen reducing configuration when heated to a temperature above body temperature.

OBJECTS AND SUMMARY OF THE INVENTION

The tissue segmentation device according to the present invention provides an apparatus and method for tissue reduction whereby tissue specimens can be removed by less invasive techniques. The device overcomes the drawbacks of the known methods by providing tissue samples which are suitable for pathology. The device incorporates a tissue isolation bag and one or more cutters which may be drawn through captive tissue either by purely mechanical force, or by a combination of mechanical force and heating.

BRIEF DESCRIPTION OF THE DRAWING FIGURES

The invention will be described in greater detail with reference to the accompanying drawings in which like elements bear like reference numerals, and wherein:

FIG. 1 is an isometric view of a prior art hand operated coring device;

FIG. 2 is a side view, partly in section, of a prior art powered coring device;

DETAILED DESCRIPTION OF THE PREFERRED EMBODIMENTS

The invention relates to a new and improved device for reducing the size of tissue specimens so that such specimens can be removed from the body by a less invasive procedure. The device will be useful in the field of laparoscopic procedures involving the ramoval of significant tissue bulk.

When a tissue sample or structure, for example, a large myoma, is required to be removed from a patient's body there are currently no convenient ways of removing the tissue, particularly when it is important to retain integrity of the tissue for subsequent pathology. In the prior art it is common to increase the size of the wound site to allow retrieval. This reduces the benefit if minimally invasive surgical techniques to remove such tissues. The invention provides a device and method which overcome the drawbacks of prior methods, and which results in tissue samples which are suitable for pathology.

The invention offers considerable improvement over existing methods of removing specimens from a patient. In particular, the invention provides a mechanically or electrically activated specimen reduction device usable in conjunction with or as part of a tissue isolation bag. The device generally employs one or more cutters made from suitable high strength cutting members such as engineering polymer based fibers or cords, high tensile steel wire, or other suitable materials known to those skilled in the art. The cutters may also be heated using, e.g., RF or resistive heating methods.

Figure 3:
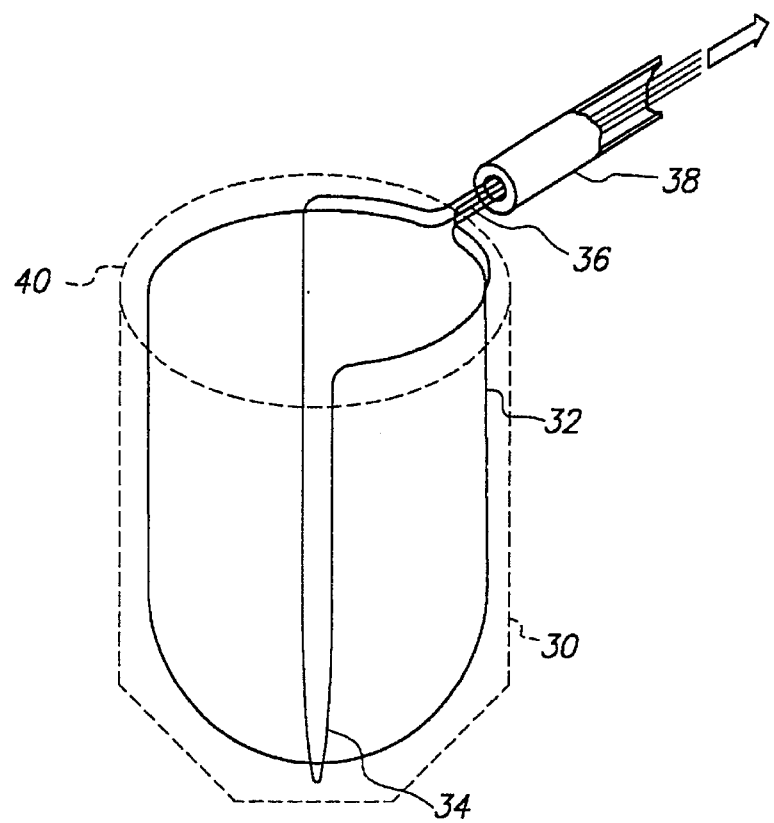
FIG. 3 is an isometric view of a first embodiment of the invention with the bag shown in phantom.

According to a first embodiment of the invention as shown in FIG. 3, the device includes a tissue isolation bag 30 containing a first loop 32 and a second loop 34 of high strength cord or wire. The tissue isolation bag 30 is preferably formed of two sheets of polymer films which are bonded together to form air spaces between the two sheets. The tissue isolation bag 30 is flexible so that it may be folded and inserted into the delivery tube 38. The bag 30 is positioned in the body in a desired location by inserting the delivery tube 38 into the body and then ejecting the bag from the delivery tube at the desired site. The bag 30 is then expanded by blowing air into the air spaces between the two layers of the bag. After the bag 30 is expanded, a tissue mass which has been surgically removed is placed inside the bag. The tissue isolation bag is then closed to contain the removed tissue and prevent escape of diseased material into the surrounding areas such as the abdominal cavity. The construction of the preferred tissue isolation bag 30 is described in U.S. Pat. No. 5,337,754 which is incorporated herein by reference, and in co-pending U.S. patent application Ser. No. 08/130,503.

The loops 32,34 are positioned along the inside surface of the bag 30 prior to the insertion of the bag into a body. The ends 36 of each of the loops 32,34 extend out of the top of the bag 30 and extend through the delivery tube 38. The ends 36 of the loops are attached to some form of pulling mechanism (not shown) at the external end of the delivery tube 38. The pulling mechanism is used to pull the ends 36 of the loops through the tube 38 reducing the loop diameter and cutting through the tissue which is trapped in the bag.

A double loop configuration with the loops positioned in planes intersecting each other at about 90°, as shown in FIG. 3, results in the captive tissue being cut into four segments. A single cutting loop may also be used and results in the captive tissue being cut into two pieces. Other numbers of loops may be used depending on the amount of cuts required so that the tissue will be divided into segments which are small enough for removal through a hole about the size of the delivery tube.

The loops 32,34 are preferably attached via bonding, or other suitable means, to the inner wall of the tissue isolation bag in such a way as to allow free access to the interior of the bag 30 for placement of the removed tissue mass. The loops may be incorporated within the wall of the isolation bag in such a manner that they break loose when placed under tension. Alternatively, the loops may be bonded to the inner surface, or may be loosely situated within the bag. When the bag is deployed using air or fluid means as described in the above referenced applications, the wires are unfolded and positioned with the unfolding of the bag.

Alternatively, the loops may be made of a shape memory alloy which is highly elastic or which has been treated to return to a particular configuration when deployed from the tube. Shape memory alloys exhibit the useful characteristic of being capable of changing physical shape upon heating above a transition temperature. For instance, a shape memory alloy wire can be formed into a memorized shape, such as that shown in FIG. 3, while in a high temperature austenitic phase. After cooling the shape memory wire to a martensitic state while maintaining the memorized shape, the wire may be plastically deformed to a different configuration in which it can be inserted into the delivery tube 38. If the wire is deployed from the delivery tube at body temperature and transforms to the austenite state, the wire can return to the memorized shape. The shape memory wires may be used to expand the tissue isolation bag instead of pressurized air.

The wires may also be deployed by the inherent springiness of the wire loops, or simply deployed manually by unrolling using graspers or the like. In all cases the cords or wires are arranged in a suitable fashion within a tissue isolation bag so as to allow easy access for the tissue to be inserted into the isolation bag.

Suitable loops may be made from, but are not limited to, fibers made from ultra high molecular weight polyethylene, Kevlar, or similar high strength polymeric materials. Alternatively, metal wires such as stainless steel, superelastic nickel titanium alloy, or resistance wire may be used for the loops.

Once the tissue has been placed in the bag 30 the neck 40 of the isolation bag 30 is drawn closed, for example, by a drawstring, to capture the tissue securely. Then the loops 32,42 are drawn progressively smaller by pulling on the ends 36 with the pulling mechanism until the loop disappears and the tissue is cut into separate pieces. An example of a suitable pulling mechanism for pulling the ends of the loops is a ratchet mounted on the delivery tube. Alternatively, a handle such as a pistol grip can be attached to the ends of the loops for manually pulling the loop ends through the tube.

Figure 4A:
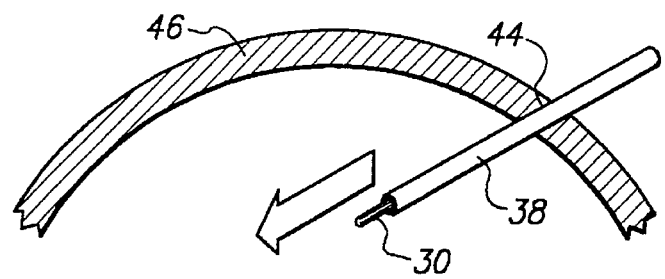
FIGS. 4a–4f are side views of the steps of removing a tissue mass from the abdominal cavity using the embodiment of FIG. 3.
Figure 4B:
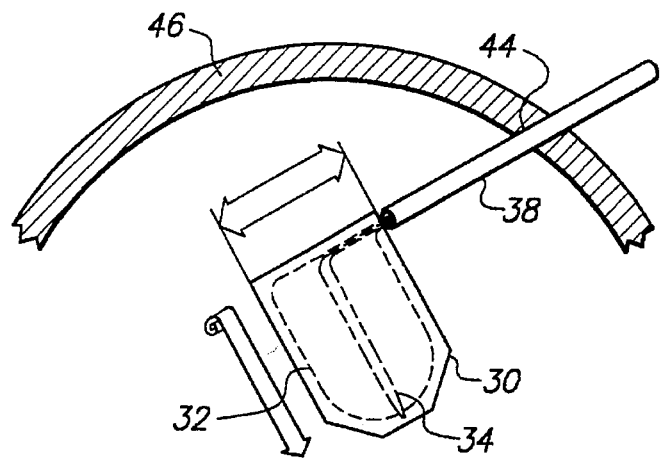
Figure 4C:
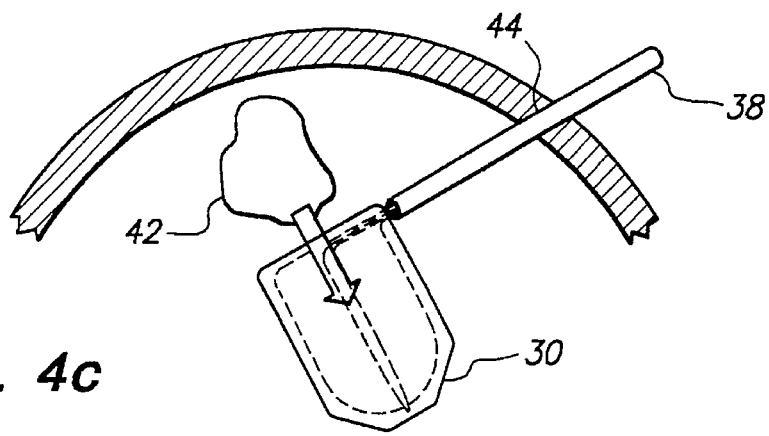
Figure 4D:
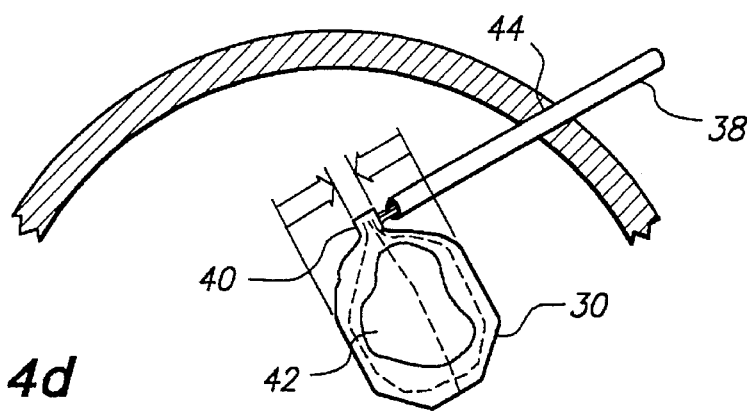
Figure 4E:
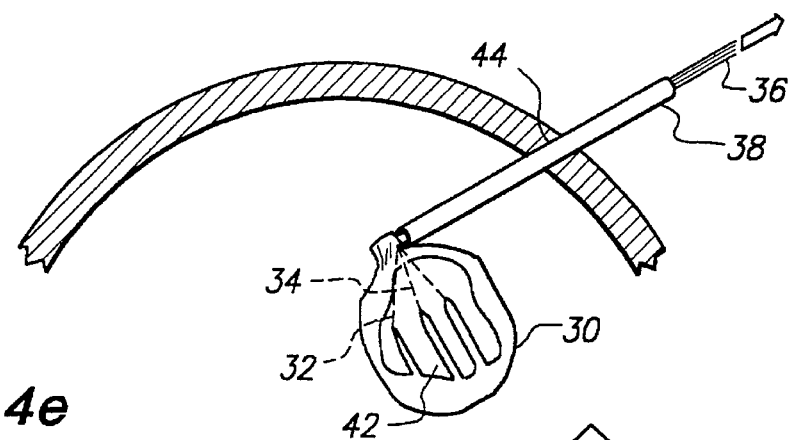
Figure 4F:
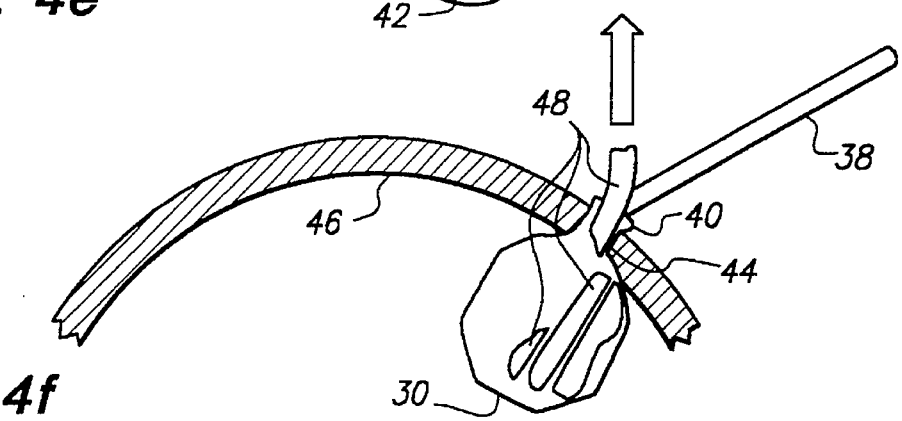

A method of removing a tissue mass using the device of the first embodiment of the invention is shown in FIGS. 4a–4f. In the first step, as shown in FIG. 4a, a small opening 44 is made in the skin 46 of the patient and the delivery tube 38 containing the compressed tissue isolation bag 30 is inserted into a body cavity such as an abdominal cavity. The bag 30 is then deployed as shown in FIG. 4b by blowing air into the spaces between the layers of the bag or by another of the expansion methods described above. FIG. 4c shows a tissue mass 42 being inserted into the bag 30. The neck 40 of the bag 30 is then closed, as shown in FIG. 4d, by pulling a drawstring (not shown) in the neck of the bag. FIG. 4e shows the segmentation of the tissue mass 42 by pulling on the ends 36 of the loops 32,34. Finally, as shown in FIG. 4f, the neck 40 of the bag 30 is brought through the skin 46 and opened so that the tissue segments 48 may be removed one at a time through the neck. This process allows a large tissue mass 42 to be removed through a much smaller opening 44 in the skin.

Figure 5:
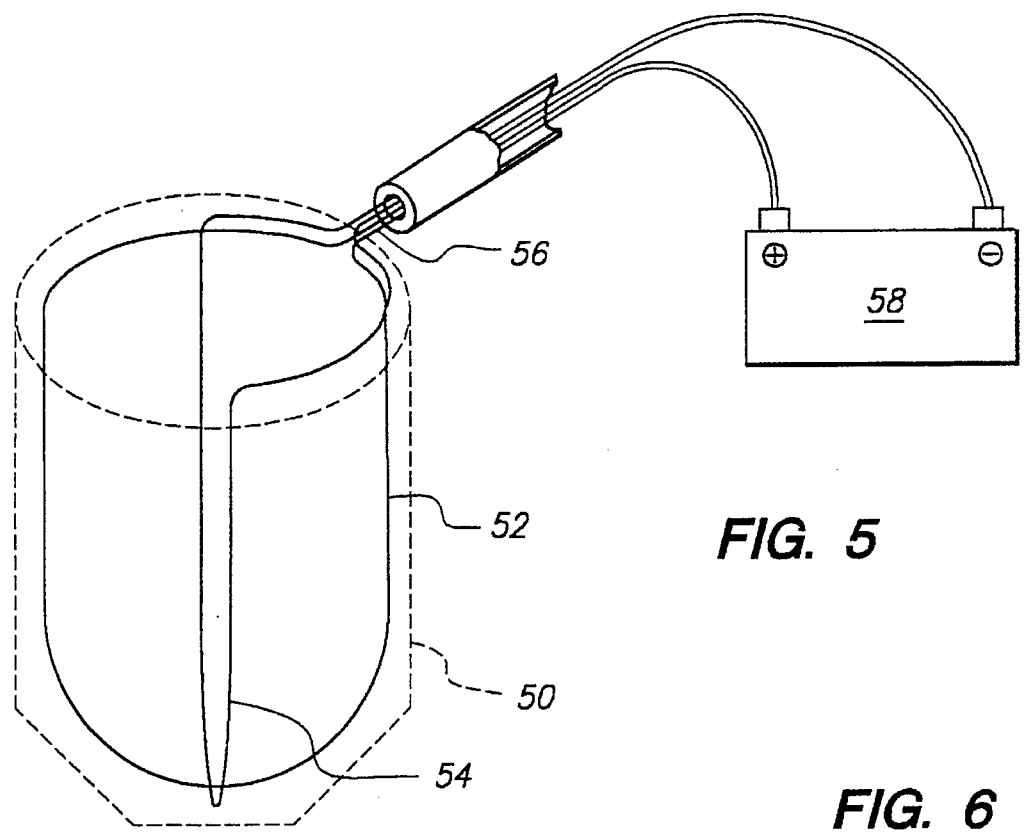
FIG. 5 is an isometric view of a second embodiment of the invention using resistive heating to aid cutting.

According to a second embodiment of the invention, shown in FIG. 5, the segmentation device incorporates loops 52,54 of wire suitable for being heated resistively by attaching the ends 56 of the loops to a direct current power supply 58. If the tissue is soft or friable the loops 52,54 may cut through the tissue entirely using force alone as described in the first embodiment. However, if there is a significant amount of tough tissue in the tissue structure to be segmented, such as connective tissue, then it has been found advantageous to heat the loops for improved cutting. The loops 52,54 may be heated by resistance heating or by attaching them to an electrocautery power unit. In the embodiment of FIG. 5, the wire loops used are preferably high strength stainless steel wire, however, other metals or metal alloys having high strength and electrical resistivity, may also be used. The embodiment of FIG. 5 is able to cut even the toughest of tissues cleanly and with extreme ease.

In the embodiment shown in FIG. 5, it is advantageous to line the tissue isolation bag walls 50 with a heat resistant and/or electrically insulating cloth, such as Kevlar or Nomex, which prevents accidental cutting or puncturing of the bag by the heated wire loops 52,54. In order to prevent short circuiting of the wire loops 52, 54 within the delivery tube, the wire loops can be insulated such that the uninsulated portions do not begin cutting the tissue until the wires have embedded substantially into the tissue.

Figure 6:
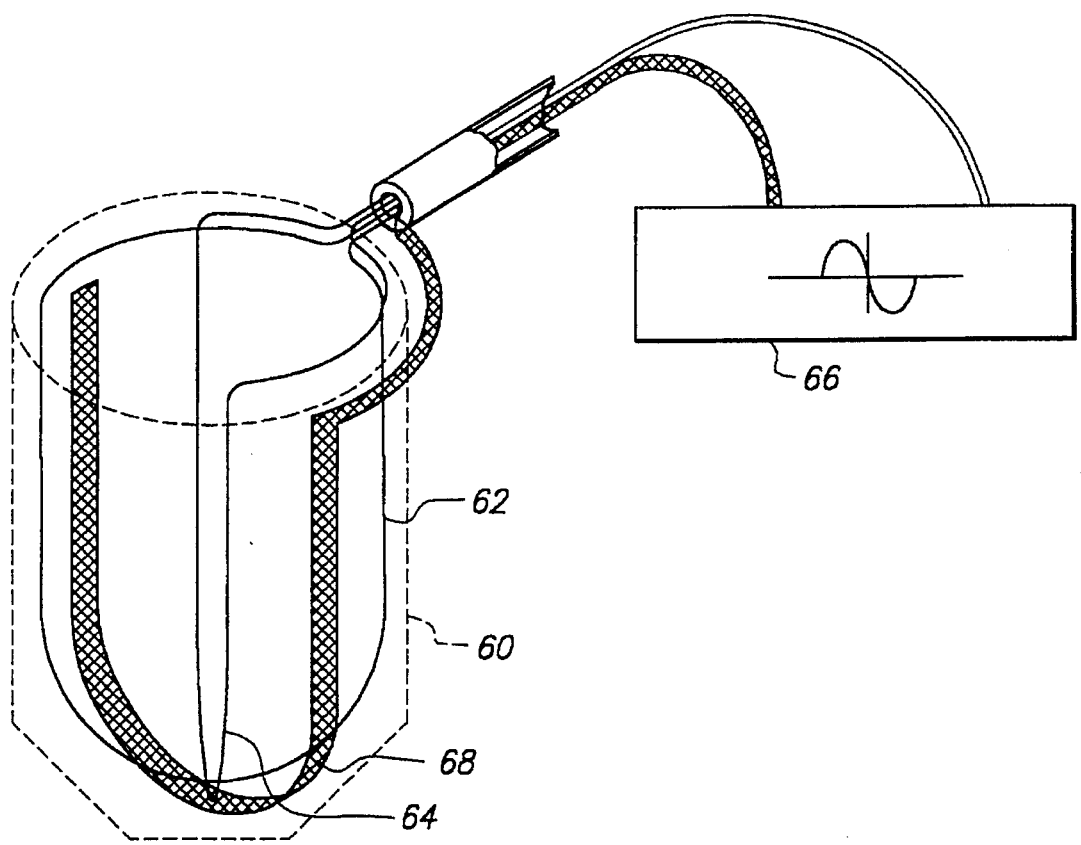
FIG. 6 is an isometric view of a third embodiment of the invention suitable for attachment to an electrocautery power supply unit, and a ground plane.

As shown in FIG. 6, a third embodiment of the invention includes wire loops 62,64 which are attached to an electrocautery power supply 66 of the type used in a hospital operating room. In this embodiment it is advantageous to have one or more ground planes 68 of electrically conductive material contained within the isolation bag 60 and arranged such that the circuit is completed by the tissue being cut. This enables the resistance heated wires to progress through the tissue without losing circuit integrity.

The ground plane 68, is shown in FIG. 6 as a U-shaped strip extending along the interior of the isolation bag 60 and connected to the electrocautery power supply through the delivery tube. Such ground planes 68 may be incorporated in a number of ways known to those skilled in the art. For instance, the ground plane can be made from aluminized plastic foil, conductive polymer or wire mesh. Alternatively, the interior of the tissue isolation bag 60 may be used as the ground plane by vapor depositing a metal coating such as aluminum directly thereon in any suitable pattern such as one or more thin strips. This particular construction ensures that the integrity of the bag is not jeopardized at any time, in that should the wires impinge on the ground plane directly the aluminum coating is totally destroyed locally and power is cut-off, preventing any intense localized heating which might burn through the bag. As long as the wire loops 62,64 are within the tissue mass, the power density transmitted to the foils is much lower, due to the large contact area of the tissue with the foil. Hence efficient cutting of the tissue is maintained, the ground plane remains intact, and the bag is not damaged. Other means of electrically grounding the contents of the isolation bag will be apparent to those skilled in the art.

Figure 7:
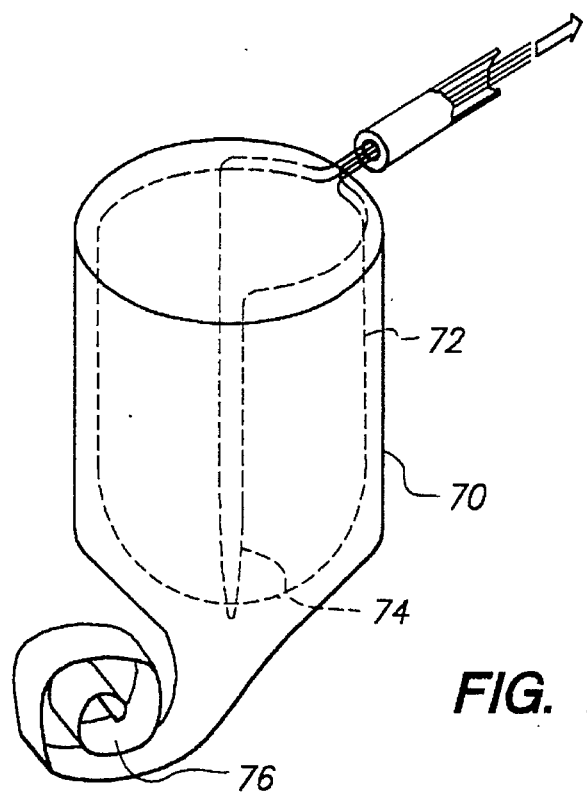
FIG. 7 is an isometric view of a fourth embodiment of the invention with a extendable bag.
Figure 8A:
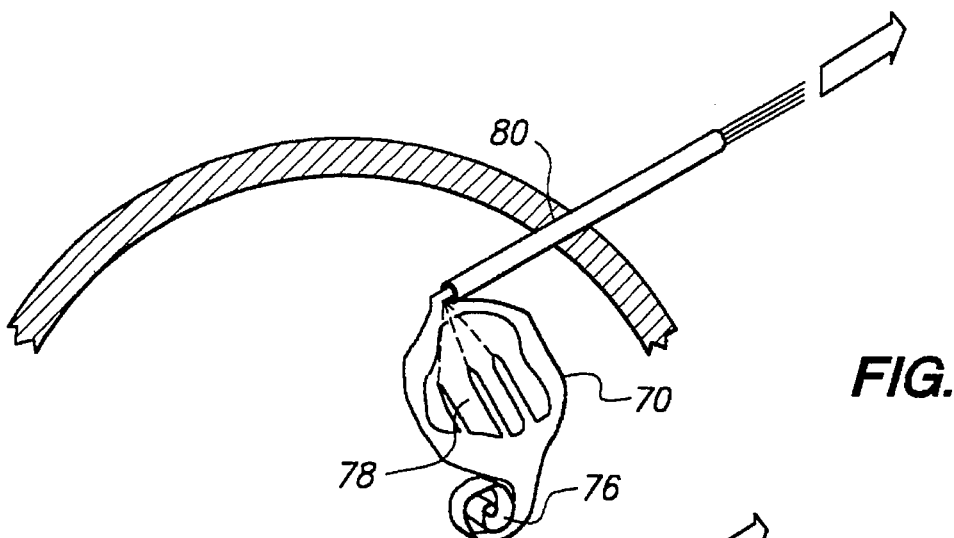
FIGS. 8a and 8b are side views of the steps of removing a tissue mass from the abdominal cavity using the embodiment of FIG. 7.
Figure 8B:
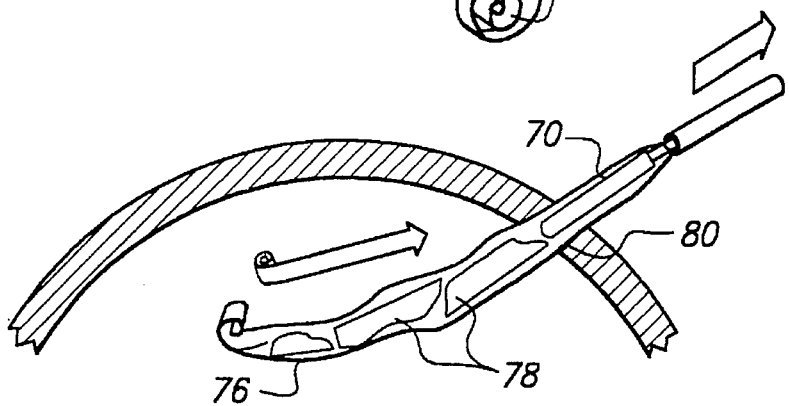
Figure 9:
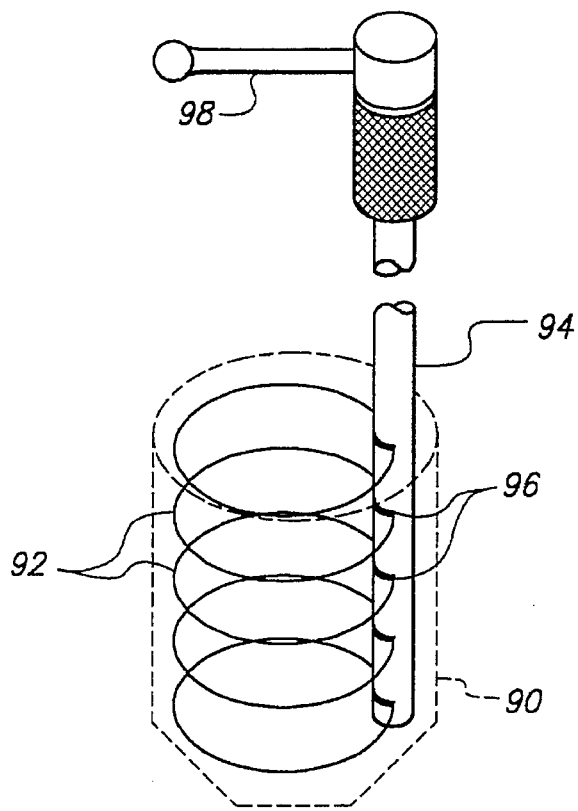
FIG. 9 is an isometric view of a fifth embodiment of the invention with an alternate arrangement of cutting loops.

A fourth embodiment of the invention including a tissue isolation bag 70 with a long, tubular extension 76 is shown in FIG. 7. This extension 76 is flexible enough to allow it to be rolled up for insertion, yet is not distendable radially. In operation, the segmentation of the tissue 78 is performed, as shown in FIG. 8a, in the same manner as in the previous embodiments. Thereafter the individual segments of tissue are shaken down into the extension, as shown in FIG. 8b. The relatively small diameter of the extension 76 ensures that the segments enter the extension individually, and are organized in a substantially linear fashion. This arrangement allows the removal of the bag 70 with the contents contained therein through the puncture site 80, rather than individually through the neck of the bag as in the previous embodiments.

A fifth embodiment of the invention, shown in FIGS. 9 and 10a–10c, employs a tissue isolation bag 90 with a series of substantially parallel wire loops 92. This embodiment is provided with a hollow shaft 94 having a series of slits 96 in the shaft perpendicular to the axis of the shaft. The loops 92 are arranged in parallel planes with the ends of the loops extending through the silts 96 into the interior of the hollow shaft 94. The tissue isolation bag 90 is positioned over a portion of the shaft 94 with the loops 92 arranged along the interior of the bag. A rotatable handle 98 is provided at the top of the shaft 94 and connected to a rod (not shown) which extends through the hollow shaft. The ends of the loops 92 are attached to the rod so that rotation of the handle 98 causes the loops to be reduced in diameter.

Figure 10A:
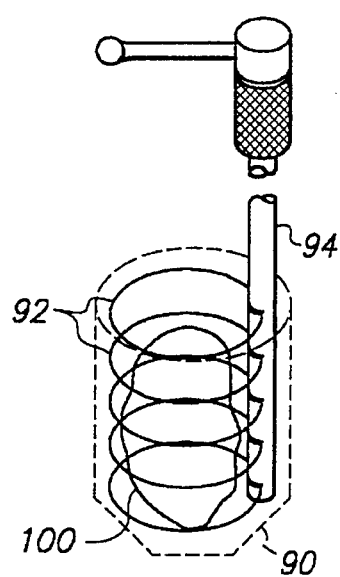
FIGS. 10a–10c are isometric views of the steps of segmentation of a tissue mass using the embodiment of FIG. 9.
Figure 10B:
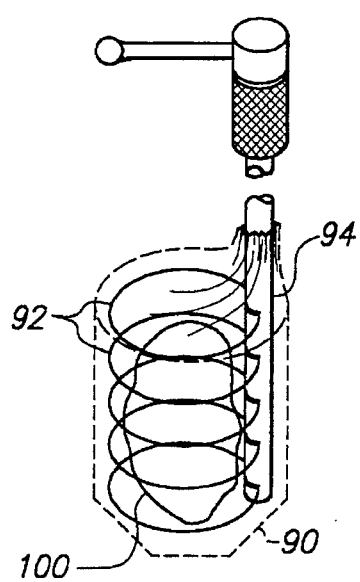
Figure 10C:
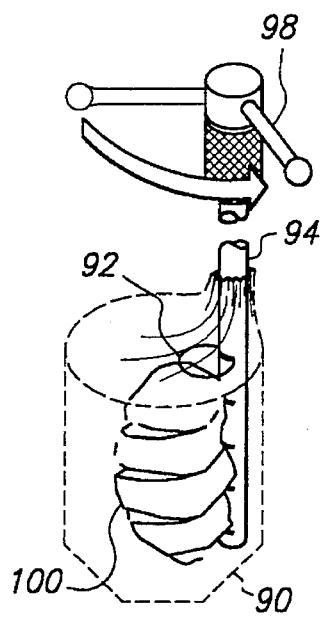

The operation of the fifth embodiment is shown in FIGS. 10a–10c. As shown in FIG. 10a, the tissue specimen 100 is placed within the bag 90 which has been inserted into the patient's body and expanded in any of the ways previously discussed. Then, the neck of the bag 90 is closed about the shaft 94, as shown in FIG. 10b. The handle 98 is then rotated, as shown in FIG. 10c, which causes the loops 92 to cut through the tissue dividing the tissue into segments. The neck of the bag is then brought through the opening in the patient's skin, the shaft 94 is removed and the segments are then removed one by one from the neck of the bag.

Figure 11A:
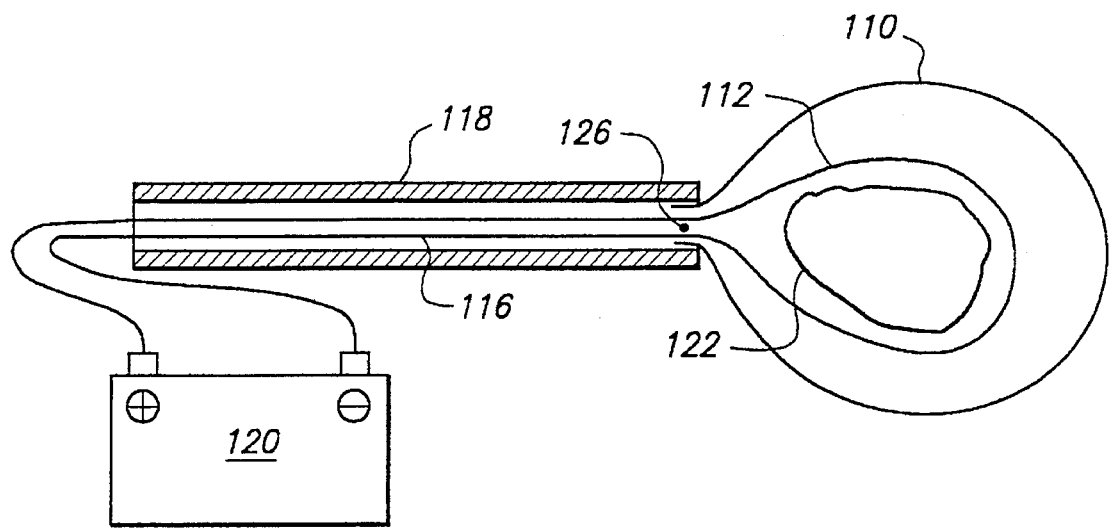
FIG. 11a is a side view, in section, of a sixth embodiment of the invention using nitinol wire loops.
Figure 11B:
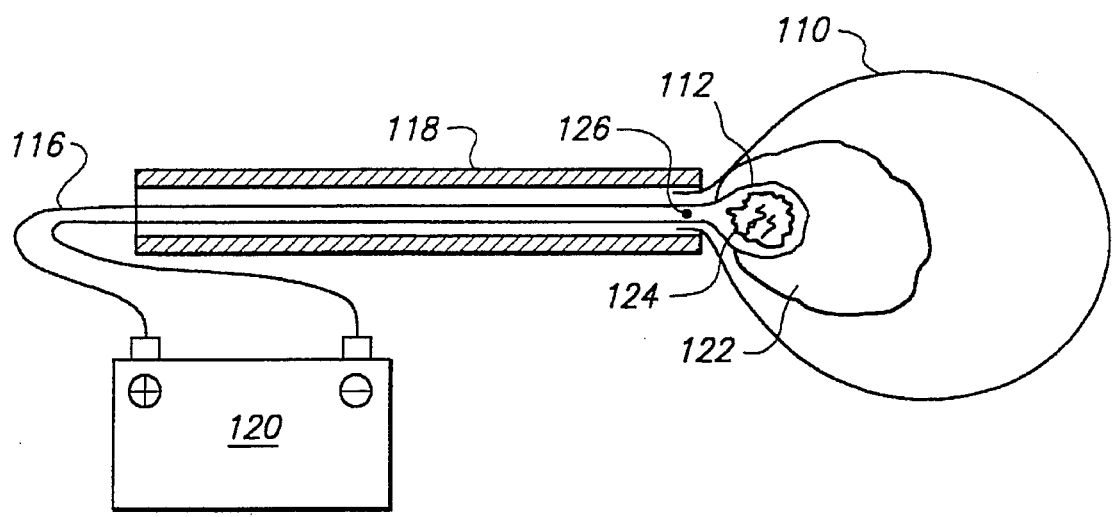
FIG. 11b is a side view in section of the embodiment of FIG. 11a prior to power application.

FIGS. 11a–11b show a sixth embodiment of the present invention including a tissue isolation bag 110 and at least one loop 112. The loop is made of nickel titanium shape memory alloy which is initially in a deformed (stretched) martensitic state. The ends of the loop extend through the delivery tube 118 and are connected via a switch to an electrical power supply 120. The wire can be caused to shrink in length by resistively heating and transforming it into its austenitic state. In operation, as shown in FIG. 11a, a tissue mass is placed within the bag 110 and the top of the bag closed. The loop 112 is cinched tight cutting through the tissue by mechanical means. Therefore, power is applied to the wire by power supply 120. The current provides resistance heating in the wire which causes the shape memory alloy loop 112 to shrink due to the transition from the martensitic state to the austenitic state, exerting great force and cutting through the tough tissue 124. The amount of shrinkage will depend on the amount the wire was previously stretched, however, a shrinkage of 7% is typical.

Figure 11C:
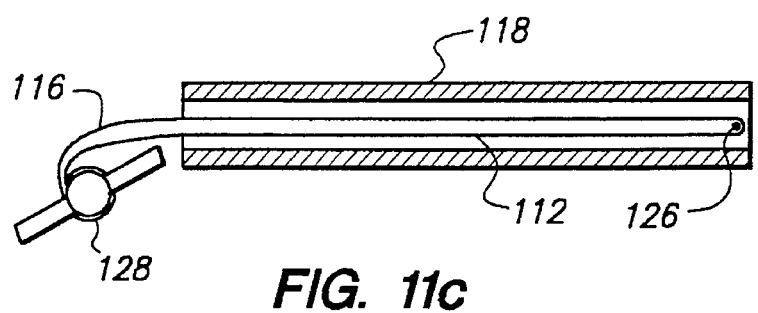
FIG. 11c is a side view of the sixth embodiment of the invention employing a restretch mechanism in order to reuse the device.

This embodiment of the invention may be reusable as shown in FIG. 11c. The delivery tube 118 is provided with a pin 126 which extends through the loop 112 and prevents the loop from being removed from the delivery tube. After the device has been used, the shape memory alloy loop 112 may be reconditioned by attaching the wires 116 to a restretch mechanism 128 such as a cam or gear whereby the loop 112 can be stretched in its martensitic condition.

The device of this invention offers a new and improved method for reducing large tissue masses to pieces small enough to be removed through a minimally invasive surgical opening such as a trocar cannula site. It further offers a method of removing such pieces and allowing for subsequent pathology due to the inherent structure of the tissue remaining substantially intact. It also offers a method of tissue reduction and removal which is extremely cost effective and fast compared to most other methods currently being used. The method requires no accessory items which are not customarily found in a standard surgical suite.

A further advantage of the tissue de-bulking device is that it can be readily folded for insertion and removal through, e.g., a standard trocar cannula. For instance, in order to remove the device from the patient the drawstring of the isolation bag can be drawn to close the bag, and the neck of the bag externalized, subsequently allowing re-opening of the neck and easy removal of the segmented tissue pieces individually.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A tissue segmentation device comprising:

a tissue isolation bag having an opened end and means for closing the opened end of the bag, the bag being capable of being introduced into a body cavity while in a collapsed state, and being expandable from the collapsed state to an expanded state when inserted into a body cavity;

at least one loop positioned within the bag, the loop having ends; and tension means for applying tension to at least one of the ends of the loop to reduce the diameter of the loop from a first diameter large enough to surround a tissue specimen placed in the bag to a second diameter small enough to cut the tissue specimen, the loop being removably secured to an inner surface of the bag, and the loop being detachable from the inner surface when tension is applied to at least one of the ends of the loop.

2. The tissue segmentation device of claim 1, wherein the tension means includes a movable member and at least one of the ends of the loop is attached to the movable member to apply tension to the loop.

3. The tissue segmentation device of claim 1, further comprising a tube for delivery of the bag into the body cavity, the loop comprising a resilient wire which expands the bag to the expanded state when the bag is ejected from an end of the tube.

4. The tissue segmentation device of claim 1, wherein the loop is formed of a shape memory alloy material.

5. A tissue segmentation device comprising:

a tissue isolation bag having an opened end and means for closing the opened end of the bag, the bag being capable of being introduced into a body cavity while in a collapsed state, and being expandable from the collapsed state to an expanded state when inserted into a body cavity;

at least one loop positioned within the bag, the loop having ends; and tension means for applying tension to at least one of the ends of the loop to reduce the diameter of the loop from a first diameter large enough to surround a tissue specimen placed in the bag to a second diameter small enough to cut the tissue specimen, the at least one loop comprising first and second loops positioned within the bag in planes substantially perpendicular to each other.

6. The tissue segmentation device of claim 1, further comprising means for applying electrical current to the loop to heat the loop to a temperature sufficient to allow cutting of the tissue specimen.

7. A tissue segmentation device comprising:

a tissue isolation bag having an opened end and means for closing the opened end of the bag, the bag being capable of being introduced into a body cavity while in a collapsed state, and being expandable form the collapsed state to an expanded state when inserted into a body cavity;

at least one loop positioned within the bag, the loop having ends; and tension means for applying tension to at least one of the ends of the loop to reduce the diameter of the loop from a first diameter large enough to surround a tissue specimen placed in the bag to a second diameter small enough to cut the tissue specimen;

means for applying electrical current to the loop to heat the loop to a temperature sufficient to allow cutting of the tissue specimen; and a ground plane comprising an electrically conductive material in contact with an inner wall of the bag, the loop and ground plane forming an electrical circuit with tissue cut by the loop.

8. The tissue segmentation device of claim 7, wherein the electrically conductive material comprises at least one of a vapor deposited coating, a conductive polymer, wire mesh, and a series of thin metal strips.

9. The tissue segmentation device of claim 1, wherein the loop is formed of a high strength engineering polymer material.

10. The tissue segmentation device of claim 1, wherein the tissue isolation bag includes a rolled-up extension at a bottom thereof, the extension being extendable for receiving segments of the tissue specimen cut by the loop.

11. The tissue segmentation device of claim 1, wherein the at least one loop comprises a plurality of loops positioned substantially parallel to each other.

12. The tissue segmentation device of claim 11, wherein each of the loops extends through a respective slot of a series of slots in a shaft extending into the tissue isolation bag.

13. The tissue segmentation device of claim 12, wherein the tension means comprises a movable member, at least one of the ends of the loops being connected to the movable member.

14. A method for tissue segmentation comprising steps of:

deploying a tissue isolation bag in a body of a patient, the tissue isolation bag including an opened end and a plurality of tissue cutting loops in an interior of the bag;

inserting a tissue specimen through the opened end and into the interior of the tissue isolation bag;

segmenting the tissue specimen into at least three pieces by applying tension to the cutting loop; and removing at least one of the pieces of the segmented tissue specimen from the bag.

15. The method of claim 14, further comprising heating the loop by passing electrical current through the loop during the segmenting step.

16. The method of claim 14, wherein the deploying step is carried out by ejecting the bag from an end of a tube, the method further comprising removing the bag from the body of the patient after the segmenting step.

17. The method of claim 15, wherein the loop comprises a shape memory alloy and the segmenting step is carried out by heating the alloy and transforming the alloy from a martensitic state thereof to an austenitic state thereof, the alloy shrinking the loop and cutting the tissue specimen during the heating.

18. The method of claim 14, wherein the segmenting step is carried out by shrinking the loop mechanically while heating the loop by passing electrical current through the loop.

* * * * *